(12) United States Patent
Jousse et al.

(10) Patent No.: US 9,920,906 B2
(45) Date of Patent: Mar. 20, 2018

(54) WHITE LED LIGHTING DEVICE AND A LIGHTING APPLIANCE

(71) Applicant: MAQUET SAS, Ardon (FR)

(72) Inventors: Robin Jousse, La Chapelle Saint Mesmin (FR); Cécilia Valteau, Ligny le Ribault (FR); Lionel Comte, La Chapelle Saint Mesmin (FR)

(73) Assignee: Maquet SAS, Ardon (FR)

(*) Notice: Subject to any disclaimer, the term of this patent is extended or adjusted under 35 U.S.C. 154(b) by 290 days.

(21) Appl. No.: 13/793,288

(22) Filed: Mar. 11, 2013

(65) Prior Publication Data

US 2013/0258661 A1    Oct. 3, 2013

(30) Foreign Application Priority Data

Mar. 27, 2012    (FR) ...................... 12 52735

(51) Int. Cl.
*F21V 11/00*    (2015.01)
*F21V 9/10*    (2006.01)
(Continued)

(52) U.S. Cl.
CPC ............... *F21V 9/10* (2013.01); *F21V 14/08* (2013.01); *F21V 23/003* (2013.01);
(Continued)

(58) Field of Classification Search
CPC .... F21V 14/08; F21V 14/085; F21V 33/0068; F21V 9/00; F21V 9/04; F21V 9/06;
(Continued)

(56) References Cited

U.S. PATENT DOCUMENTS 5,893,626 A * 4/1999 Poling .............................. 362/35
5,969,868 A * 10/1999 Bornhorst ................. F21V 9/08
359/589
(Continued)

FOREIGN PATENT DOCUMENTS

DE    10 2006 040393    3/2008
EP    1 462 711    9/2004
(Continued)

OTHER PUBLICATIONS

Lee Lighting'001, Jan. 11, 2012, Colour Effect Filters, https://web.archive.org/web/20120111104853/http://www.leefilters.com/lighting/colour-list.html.*
(Continued)

*Primary Examiner* — Bryon T Gyllstrom
*Assistant Examiner* — James Endo

(57) ABSTRACT

An LED lighting device (6) having an LED (8) emitting white light and optical filter means (12) suitable for filtering the white light emitted by the LED (8). The optical filter means comprise at least two optical filters (12) that have different transmission coefficients and that are positionable to filter the light emitted by the LED (8) individually. The lighting device (6) includes a power supply unit (10) suitable for delivering different power supply currents to the LED (8) depending on whether one or the other of the optical filters (12) is positioned to filter the light from the LED (8), so as to modify the color temperature of the light emitted by the LED (8).

12 Claims, 3 Drawing Sheets

(51) Int. Cl.
*F21V 14/08* (2006.01)
*H05B 33/08* (2006.01)
*F21V 33/00* (2006.01)
*F21V 23/00* (2015.01)
*F21S 10/00* (2006.01)
*A61B 1/06* (2006.01)
*F21V 9/00* (2018.01)
*F21V 9/08* (2018.01)
*F21S 10/02* (2006.01)
*F21V 9/04* (2018.01)
*F21V 9/06* (2018.01)
*F21W 131/205* (2006.01)
*F21Y 115/10* (2016.01)

(52) U.S. Cl.
CPC ..... *F21V 33/0068* (2013.01); *H05B 33/0857* (2013.01); *A61B 1/0646* (2013.01); *F21S 10/007* (2013.01); *F21S 10/026* (2013.01); *F21V 9/00* (2013.01); *F21V 9/04* (2013.01); *F21V 9/06* (2013.01); *F21V 9/08* (2013.01); *F21W 2131/205* (2013.01); *F21Y 2115/10* (2016.08)

(58) Field of Classification Search
CPC . F21V 9/10; F21V 5/048; F21V 5/046; F21V 9/08; F21W 2131/205; F21S 10/007; F21S 10/026; A61B 1/0646; F21L 15/04
USPC ......... 362/293, 804, 238, 239, 242, 249.03, 362/572, 573; 359/888
See application file for complete search history.

(56) References Cited

U.S. PATENT DOCUMENTS

| | | | | |
|---|---|---|---|---|
| 6,113,252 A * | 9/2000 | Arlitt | ........... | F21S 8/02 362/268 |
| 6,474,837 B1 * | 11/2002 | Belliveau | ........... | 362/231 |
| 6,796,683 B2 * | 9/2004 | Wood | ........... | F21S 10/02 362/268 |
| 7,052,146 B2 * | 5/2006 | Esterberg | ........... | G03B 21/14 353/119 |
| 7,163,317 B2 * | 1/2007 | Warnecke | ........... | F21S 10/02 362/230 |
| 7,452,105 B2 * | 11/2008 | Hough | ........... | F21V 5/04 362/268 |
| 7,457,063 B2 * | 11/2008 | Kao | ........... | G02B 26/008 359/889 |
| 7,682,042 B2 * | 3/2010 | Feinbloom et al. | ..... | 362/249.03 |
| 7,980,738 B2 * | 7/2011 | Chiang | ........... | 362/427 |
| 2002/0149941 A1 * | 10/2002 | Mateescu et al. | ........... | 362/293 |
| 2003/0107893 A1 * | 6/2003 | Dho | ........... | G02B 26/008 362/293 |
| 2003/0137844 A1 * | 7/2003 | Bucher | ........... | F21S 10/007 362/293 |
| 2004/0105261 A1 * | 6/2004 | Ducharme | ........... | H05B 33/0857 362/231 |
| 2004/0201828 A1 * | 10/2004 | Wang | ........... | G02B 27/0927 353/84 |
| 2005/0231945 A1 * | 10/2005 | Leibinger et al. | ........... | 362/231 |
| 2007/0019408 A1 * | 1/2007 | McGuire, Jr. | ........... | F21S 10/007 362/231 |
| 2008/0062681 A1 * | 3/2008 | Belliveau | ........... | F21S 10/007 362/231 |
| 2008/0259589 A1 * | 10/2008 | Van De Ven | ........... | F21K 9/00 362/84 |
| 2009/0086475 A1 * | 4/2009 | Caruso et al. | ........... | 362/231 |
| 2009/0187234 A1 * | 7/2009 | Meyer | ........... | C09K 11/06 607/88 |
| 2009/0227847 A1 * | 9/2009 | Tepper et al. | ........... | 600/249 |
| 2009/0273763 A1 * | 11/2009 | Kjaer | ........... | G03B 21/14 353/84 |
| 2010/0002428 A1 * | 1/2010 | Hall | ........... | F21V 5/008 362/231 |
| 2010/0073934 A1 * | 3/2010 | Ho | ........... | F21L 15/02 362/311.1 |
| 2010/0081887 A1 * | 4/2010 | Marka et al. | ........... | 600/249 |
| 2010/0085758 A1 * | 4/2010 | Takahashi et al. | ........... | 362/293 |
| 2010/0210918 A1 * | 8/2010 | Dunn et al. | ........... | 600/249 |
| 2011/0228515 A1 * | 9/2011 | Grajcar | ........... | A01K 1/00 362/84 |
| 2012/0043915 A1 * | 2/2012 | Rohwedder | ........... | F21V 21/40 315/362 |
| 2012/0162993 A1 * | 6/2012 | Cheng et al. | ........... | 362/284 |
| 2012/0206922 A1 * | 8/2012 | Feklistov | ........... | G02B 27/0927 362/311.12 |
| 2012/0307388 A1 * | 12/2012 | Bornhorst | ........... | G02B 26/008 359/888 |
| 2012/0327631 A1 * | 12/2012 | Tsang | ........... | F21V 9/10 362/84 |
| 2012/0327663 A1 * | 12/2012 | Doan | ........... | F21V 9/08 362/294 |
| 2013/0093362 A1 * | 4/2013 | Edwards | ........... | 315/313 |

FOREIGN PATENT DOCUMENTS

| | | |
|---|---|---|
| GB | 2 430 248 | 3/2007 |
| GB | 2 472 694 | 2/2011 |
| JP | 1999-178839 | 7/1999 |
| JP | H11178839 A | 7/1999 |
| KR | 10-2004-0067759 | 7/2004 |
| WO | 2008/087404 | 7/2008 |

OTHER PUBLICATIONS

Lee Lighting'002, 206 and 208 Colour Filters, http://www.leefilters.com/lighting/colour-details.html#206&sort=number.*

* cited by examiner

WHITE LED LIGHTING DEVICE AND A LIGHTING APPLIANCE

CROSS REFERENCE TO RELATED APPLICATION

This application claims priority under 35 USC § 119 to French Patent Application No. 12 52735 filed on Mar. 27, 2012, which application is hereby incorporated by reference in its entirety.

TECHNICAL FIELD

The invention relates to a light-emitting diode (LED) lighting device having an LED emitting white light and optical filter means suitable for filtering said white light emitted by the LED.

The invention also provides a lighting appliance for an operating theater including such a lighting device.

PRIOR ART

More particularly, the invention applies to a lighting device intended mainly for use in a medical situation, in particular in an operating theater. Such a lighting device needs to enable a surgeon to operate under good conditions, and in particular to distinguish correctly between the various types of tissue. For this purpose, the lighting device needs to comply with certain standards and to produce light that is generally white, presenting a color rendering index (RCI) lying in the range 85 to 100. In addition, the color temperature of the light produced by the lighting device must lie in the range 3000 K (warm colors) and 6700 K (cool colors), in accordance with the standard IEC 60601-2-41, so as to enable the surgeon to distinguish small color differences without effort.

The term "color temperature" as applied to light is used to mean the equivalent color temperature evaluated, in well-known manner, as are the chromatic coordinates (x,y), on the basis of the spectrum of the light in a reference chromatic diagram of the International Commission on Illumination (CIE).

A distinction is made between the light flux from a light source, which is the light power it emits expressed in lumens, and the visual illumination provided by a lighting device in an illuminated field, which is the quantity of light flux lighting the illuminated field expressed in lux, i.e. in lumens per square meter ($lm/m^2$).

Depending on the operation to be performed, the surgeon may have a wide variety of lighting needs and those needs may even vary as the operation progresses. That is why it is desirable for the surgeon to be able to modify the spectral characteristics of the light produced by the lighting device, such as its color temperature or the chromatic coordinates, so as to obtain different colors of white that are appropriate for the operation.

At present, various different types of lighting device are in existence that satisfy the lighting requirements of medical conditions that use a mixture of white LEDs and of color LEDs in order to obtain white lighting at a desired color temperature, but none of them proposes a lighting device having a modifiable spectral characteristic.

For example, patent document DE 10 2006 040393 discloses an LED lighting device that produces white illuminating light from LEDs emitting cool white light, warm white light, red light, and green light. That device makes use in particular of an optical filter placed directly on an LED emitting cold white light in order to obtain warm white light. However, the color temperature and the illuminating light emitted by the lighting device are not modifiable. It is also known that filters reduce the light flux of the illuminating light, which is not desirable.

Also known is patent document WO 2008/087404, which discloses a lighting device that produces white illuminating light from white LEDs and red LEDs. By using an optical filter placed in front of the white LEDs, that lighting device enables a desired color temperature to be obtained for the illuminating light. Nevertheless, that lighting device does not enable the surgeon to modify the color temperature of the illuminating light.

A drawback of those two prior devices lies in the fact that when an obstacle is masking a fraction of the light flux (e.g. when the surgeon leans over), then the balance between the contributions of the various colored LEDs is lost, thereby modifying the color temperature of the light produced by the lighting device, producing a rainbow effect, and forming colored shadows in the illuminated field.

SUMMARY OF THE INVENTION

The object of the invention is to remedy all those drawbacks by proposing an LED lighting device that produces white illuminating light in an illuminated field having spectral characteristics, such as for example color temperature, that are adjustable by the surgeon without reducing the visible illumination in the illuminated field.

To this end, the invention provides an LED lighting device having an LED emitting white light and optical filter means suitable for filtering said white light emitted by the LED, the device being characterized in that said optical filter means comprise at least two optical filters that have different transmission coefficients and that are positionable to filter said light emitted by the LED individually, and in that the lighting device includes a power supply unit suitable for delivering different power supply currents to said LED depending on whether one or the other of the optical filters is positioned to filter said light from the LED, so as to modify the color temperature of the light emitted by the LED.

With such an arrangement of the lighting device of the invention, the spectral characteristics of the illumination in the illuminated field, in particular the color temperature or the chromatic coordinates and thus the white color, are easily adjustable, merely by changing the optical filter without modifying the visual illumination in the illuminated field, since the light flux from the LED is conserved by varying the power supply to the LED.

Another advantage of the lighting device of the invention is that by using white LEDs only, the color temperature that is obtained is not modified in the presence of an obstacle in the light flux.

For example, the lighting device of the invention may advantageously include at least one optical filter suitable for attenuating a red component of the light emitted by the LED so as to attenuate the energy delivered by the LED, i.e. reduce its radiant energy. Such an optical filter, also referred to as a "cold" filter, serves to block the longest wavelengths while remaining neutral in terms of color perception by the human eye in the visible domain, i.e. such a filter modifies neither the color temperature nor the color rendering index of the light produced by the lighting device.

With the lighting device of the invention, it is thus possible to reduce the radiant energy from the light source, which is both a source of drying so far as the patient is concerned and of inconvenience for the medical staff. It should be recalled that radiant energy is conventionally defined as the ratio of energy intensity expressed in watts per square meter (W/m²) and illuminance expressed in lux. Energy intensity covers all radiation in the range 300 nanometers (nm) to 2500 nm. By way of comparison, visual illuminance covers illumination in the range 360 nm to 780 nm and it is weighted by the sensitivity of the eye, which is practically zero beyond 700 nm. A "cold" optical filter as described above thus enables energy intensity to be lowered without modifying visual illuminance and without affecting either the color temperature nor any other colorimetric properties.

Advantageously, the lighting device of the invention may include at least one optical filter suitable for attenuating a blue component of the light emitted by the LED at a wavelength lying in the range 400 nm to 480 nm. Such an optical filter, referred to herein as a "blue" filter, serves to provide illumination of the illuminated field that is balanced over all visible wavelengths and that provides very good color perception for the surgeon, and limiting photobiological risks.

It is known that LEDs, and in particular white LEDs, possess in their emission spectrum a high proportion of blue component, commonly referred to as the "blue peak". Such unbalance in the components of the white light emitted by LEDs affects color perception by the surgeon. In addition, it is known that excess blue components, in the meaning of the standard EN62471, increases photobiological risk. FIG. 1 shows an example of the emission spectrum of a white LED, i.e. the relative intensity I emitted by the LED as a function of the wavelength of the light emitted by the LED. The example of FIG. 1 shows clearly, identified by arrow P, the presence in the emission spectrum of a blue peak at short wavelengths lying in the range about 400 nm to 480 nm, and centered around 450 nm.

A "blue" optical filter as defined above makes it possible to attenuate light in a wavelength range that presents the greatest blue photobiological risk, as defined for example in standard EN62471: 2008. In addition, such a "blue" optical filter advantageously makes it possible to reduce the color temperature of the light produced by the lighting device, thereby providing the surgeon with the option of varying the color temperature of the lighting in simple and easy manner in order to adapt it to requirements.

A lighting device of the invention may advantageously present the following features:
   the lighting device comprises a plurality of consecutive optical filters having progressive transmission coefficients for attenuating the blue component;
   the attenuation difference between two consecutive optical filters is at least 15%;
   the lighting device has a plurality of identical LEDs, each emitting white light;
   each LED is associated with a set of optical filters having different transmission coefficients, the sets of optical filters being identical from one LED to another;
   said optical filters are arranged on a rotary disk; and
   said filters are arranged at the periphery of said rotary disk.

The invention also extends to a lighting appliance for an operating theater including at least one such lighting device.

BRIEF DESCRIPTION OF THE DRAWINGS

The present invention can be better understood and other advantages appear on reading the detailed description of an embodiment taken by way of non-limiting example and shown in the accompanying drawings, in which.

DESCRIPTION OF EMBODIMENTS

Figure 2:
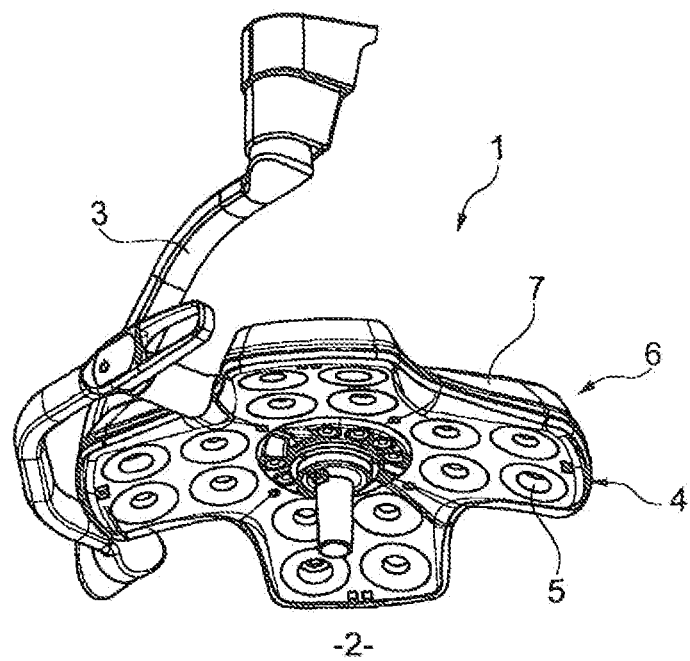
FIG. 2 is a diagrammatic perspective view of a lighting appliance comprising four lighting devices of the invention.

FIG. 2 shows a lighting appliance 1 lighting an illuminated field 2, here a field where a surgeon is operating on a patient.

The lighting appliance 1 is of the type that is suspended from the ceiling of the operating theater in known manner, and it comprises a hinged suspension arm 3 carrying an overhead light 4.

As can be seen in FIG. 2, the light 4 is in the form of a cross in which each of its branches comprises a lighting device 6 of the invention inserted in a housing 7 of the light 4. As an example, the lighting devices 6 are substantially identical, each of them having four substantially identical lighting outlets 5.

Advantageously, the lighting devices 6 have LEDs 8 arranged to emit white light, and preferably each lighting outlet 5 has only one white LED 8. By way of example, the LED 8 emits white light with a color temperature of 5000 K.

Figure 3:
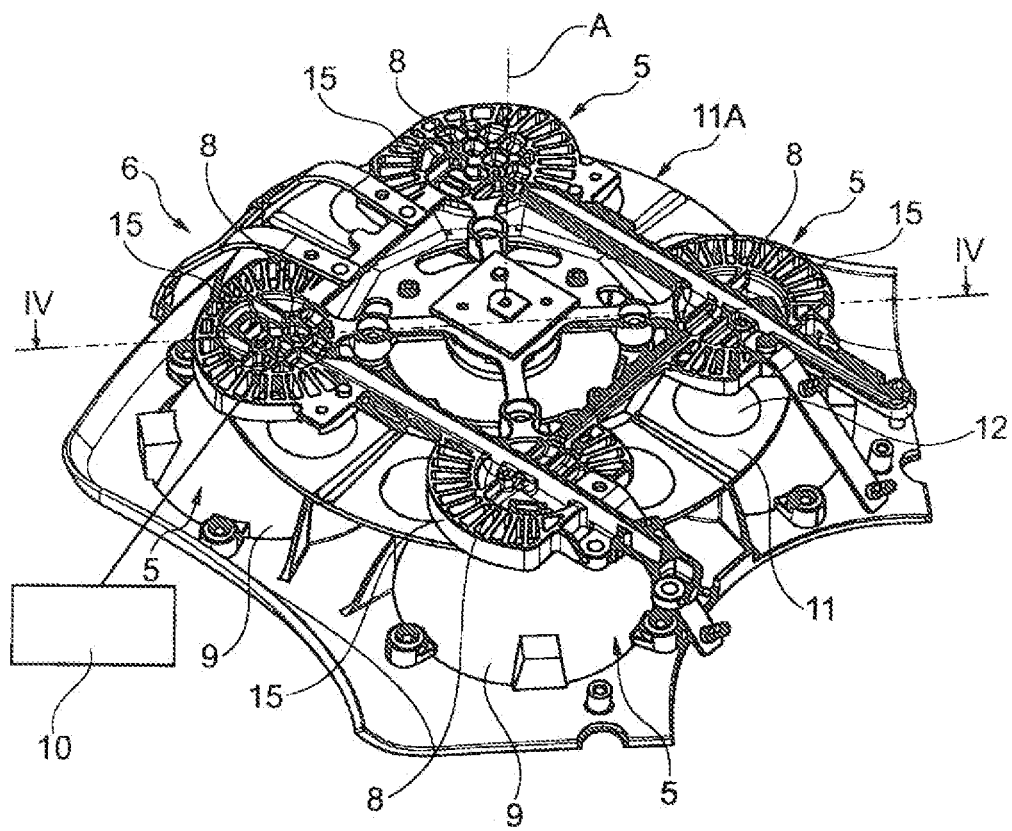
FIG. 3 is a diagrammatic perspective view of the rear portion of one of the FIG. 2 lighting devices.

FIG. 3 is a diagrammatic enlarged view of a lighting device 6 of the invention without the housing 7 in order to show its optical elements more clearly.

As can be seen in FIG. 3, each lighting outlet 5 thus comprises the white LED 8 in front of which there is arranged a conventional collimator 9 to direct the light flux from the LED 8 towards the lighting field 2, and interposed between the collimator 9 and the LED 8, there are optical filter means 12 for filtering the light emitted by the LED 8. A radiator 15 is preferably arranged adjacent to the LED 8 in order to dissipate the heat produced by the LED 8.

Figure 4:
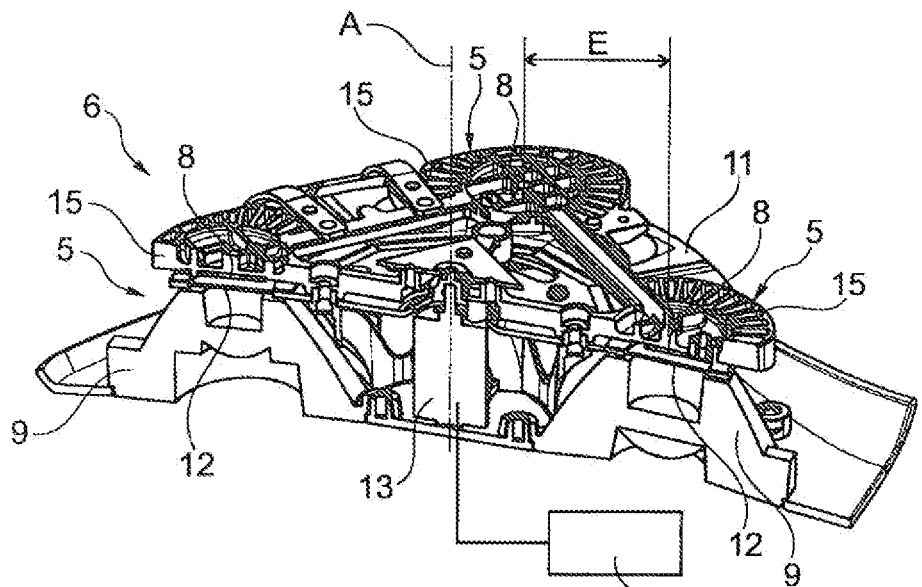
FIG. 4 is a diagrammatic section view on axis IV-IV in FIG. 3 showing a portion of the FIG. 2 lighting device.

FIG. 4 shows the lighting device 6 in cross-section on axis IV-IV of FIG. 3 in order to show more clearly that each optical filter 12 is arranged between a LED 8 and a collimator 9, this configuration making it possible to use optical filters 12 of small size.

Advantageously, the optical filter means comprise, for each LED 8, a plurality of optical filters 12, three optical filters 12 in this example, that are arranged consecutively and that have transmission coefficients that are different and preferably progressive, which filters are positioned to filter individually the light emitted by each LED 8 so as to obtain different colors of white, i.e. so as to obtain a variable color temperature or variable chromatic coordinates.

More precisely, the lighting device 6 has a support 11 for supporting the optical filters 12 that are mounted to pivot about an axis A in such a manner that the optical filters 12 and the LEDs 8 are movable relative to one another. The support 11 in this example is in the form of a disk, with the optical filters 12 being arranged at the periphery 11A of the disk 11 and being aligned on a circle centered on the axis A, and the LEDs 8 are arranged at the four corners of a square that is inscribed in the circle formed by the optical filters 12 such that, when the disk 11 turns about the axis A, the optical filters 12 occupy successive positions in which they are in axial alignment with the LEDs 8 so that the white light emitted by those LEDs 8 passes through them. It can thus readily be understood that for each position of the disk 11 about the axis A, each LED 8 is in axial alignment with an optical filter 12, which consequently has the white light emitted by that LED 8 passing therethrough.

In addition, the LEDs 8 are powered electrically by an electrical power supply unit 10 (represented diagrammatically in this example solely for one lighting outlet 5), arranged to power each LED 8 with different and variable current levels depending on which one of the optical filters 12 is positioned in front of the LED 8 to filter its light. The power supply unit 10 may be in the form of a single power supply for all of the LEDs 8 of the lighting device 6, or it may be in the form of a plurality of power supplies respectively associated with each of the LEDs 8.

Advantageously, each time the disk 11 turns about the axis A in order to align the LEDs 8 with one specific type of optical filter 12, the power supply unit adjusts the currents passing through the LEDs 8 so as to conserve substantially constant light flux leaving the lighting device 6, i.e. so as to conserve substantially constant visual illumination in the lighting field, regardless of the type of filter that is placed in front of the LEDs 8. The term "substantially constant" is used to mean that the light flux is identical to within 5% on each change of optical filter 12.

For each position of the disk 11 about the axis A, the four LEDs 8 are preferably aligned with respective optical filters 12 of the same type, such that the lighting device 6 presents uniform light flux. For this purpose, provision may be made for the spacing between two successive LEDs 8, referenced E in FIG. 4, to be substantially equal to the spacing between two optical filters 12 of the same type forming parts of two successive sets of filters.

The optical filters 12 are preferably specified in such a manner that the minimum and maximum color temperatures obtained after attenuating the blue peak lie in the range that is authorized by the standard IEC 60601-2-41. In particular, the color temperatures that are commonly encountered in operating theaters should be selected.

By way of particular example, the disk 11 carries a total of twelve optical filters 12 arranged in four identical sets, each associated with one respective LED and each comprising three optical filters 12 of types that are different and progressive, thereby enabling three color temperatures to be obtained that are different and progressive.

The term "progressive" is used to mean that the optical filters 12 are selected so as to establish a transmission difference between two successive types of optical filter in a given set of optical filters 12, with this transmission difference preferably being at least 15%. By way of example, within a set of three optical filters associated with a LED 8, the first optical filter 12 thus has a first transmission coefficient that does not modify the color temperature and that enables a maximum color temperature to be obtained, 5000 K in this example, the second optical filter 12 has a second transmission coefficient that enables an intermediate color temperature to be obtained, 4500 K in this example, and the third optical filter 12 has a third transmission coefficient that enables a minimum color temperature to be obtained, 3900 K in this example.

Figure 5:
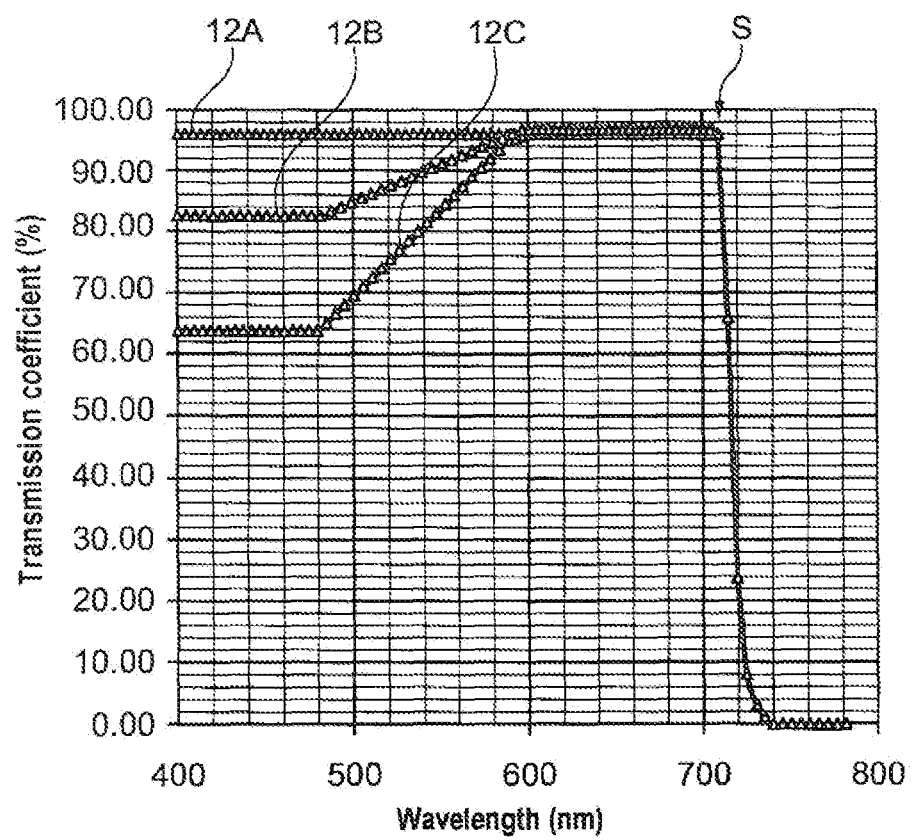
FIG. 5 shows the transmission coefficients of three optical filters of a lighting device of the invention.

FIG. 5 plots an example of the transmission coefficients 12A, 12B, and 12C of the three progressive optical filters in a set of optical filters 12 as a function of wavelength. FIG. 5 is given by way of example for an angle of incidence of the light on the filters of 30%. For some other angle of incidence, the transmission coefficients vary a little as a function of wavelength.

As can be seen in FIG. 5, the three optical filters 12A, 12B, and 12C are suitable for absorbing a red component of the light emitted by the LED 8 in order to reduce the radiant energy without modifying the color temperature and without modifying the color rendering of the light emitted by the LED 8. The drop in the radiant energy is of the order of 0.4 milliwatts per square meter per lux ($mW \cdot m^{-2} \cdot lux^{-1}$) to 0.5 $mW \cdot m^{-2} \cdot lux^{-1}$. In the example of FIG. 5, the transmission coefficients of three optical filters 12A, 12B, and 12C all present a threshold beyond which the transmission coefficient drops to reach 2% for wavelengths longer than 740 nm. This threshold is referenced S in FIG. 5, and in this example it is situated at a wavelength of about 700 nm, however it could lie in the range 670 nm to 750 nm, and it should be adapted in particular depending on the type of LED 8 used and on the angle of incidence of the light emitted by the LED 8 onto the filter.

FIG. 5 also shows that the first optical filter has a transmission coefficient of 96%±2% for wavelengths shorter than 700 nm. This first optical filter 12A thus serves to conserve the color temperature of the light emitted by the LED 8 while limiting the production of heat.

Figure 1:
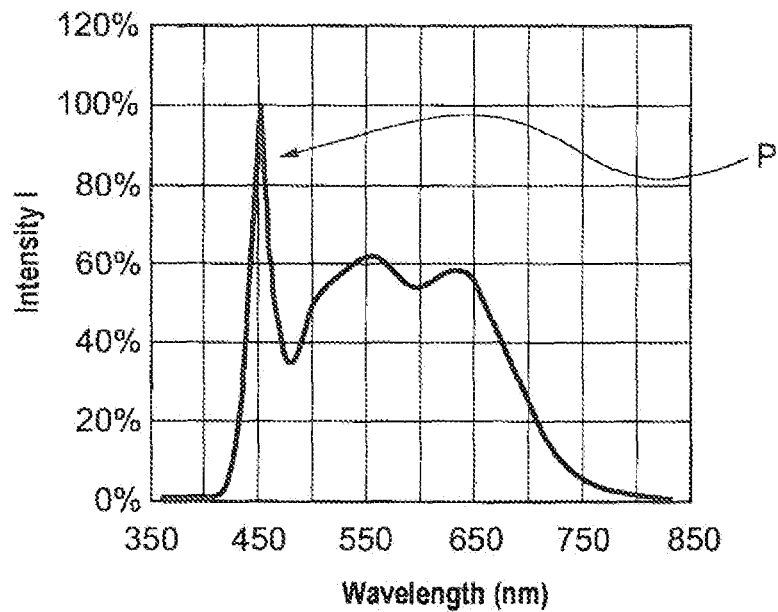
FIG. 1 is a graph showing the emission spectrum of a white LED.

Finally, FIG. 5 shows that the second and third optical filters 12B and 12C also attenuate the blue component of the white light emitted by the LED 8 and corresponding to the blue peak of the emission spectrum shown in FIG. 1, i.e. the wavelength around 450 nm, and preferably attenuating blue components at wavelengths lying in the range about 400 nm to about 480 nm.

More precisely, the second optical filter 12B has a transmission coefficient equal to 83%±2% for wavelengths lying in the range 400 nm to 480 nm, and then a transmission coefficient that increases with increasing wavelength from 83% up to 97%±2% for wavelengths lying in the range 480 nm to 620 nm. The third filter 12C has a transmission coefficient equal to 64%±2% for wavelengths lying in the range 400 nm to 480 nm, and then a transmission coefficient that increases with increasing wavelength form 64% up to 97%±2% for wavelengths lying in the range 480 nm to 620 nm. These second and third optical filters 12B and 12C thus enable the color temperature of the light emitted by the LED 8 to be modified, each of them reducing the color temperature by 600 K, while also limiting the production of heat. Thus, the optical filter means 12 enable the color temperature of the light emitted by the LED 8 to be modified.

Depending on the application, the optical filters 12 may be made of glass or of plastics material. The optical filters 12 are preferably fabricated by depositing thin films under a vacuum or by a sol-gel technique, onto a transparent substrate.

The disk 11 carrying the optical filters 12 may advantageously be turned by a motor 13 controlled by a control unit 14 shown in FIG. 4, so that the surgeon can change the optical filters 12 simply and quickly by acting on the control unit 14.

The LEDs 8 of the lighting outlets 5 are preferably substantially identical to one another so as to avoid any differences in light flux and/or spectrum in the visible range from one lighting outlet 5 to another. In particular, it is preferable for the LEDs 8 to be selected so that they come from the same supplier, e.g. having the same type of phosphorous-based component, the same package, the same electronic chip, and requiring the same type of power supply. White LEDs 8 should be selected that have a high color rendering index, lying in the range 85 to 100, preferably lying in the range 90 to 100, or indeed in the range 95 to 100, and a color temperature lying in the range 3000 K to 6700 K in order to comply with the standards in force concerning lighting in medical situations.

Naturally, the present invention is not limited to the above description of a single embodiment thereof, and it may be subjected to various modifications without thereby going beyond the ambit of the invention.

For example, it is naturally possible to have some other number of optical filters 12 associated with each LED in the lighting device 6. It is also possible to have some other number of LEDs 8 and of lighting outlets 5 in the lighting device 6. Finally, some other number of lighting devices 6 may be provided in each overhead light 4. The cross-shape for the light 4 is given purely by way of example.

By way of example, it is possible to use a LED that emits white light at a low color temperature, e.g. 3000 K. Under such circumstances, the optical filters 12 should be selected so as to be capable of increasing the color temperature of the light, e.g. by attenuating red components of the light in the range 600 nm to 700 nm.

Provision may also be made to use other types of optical filter, e.g. that attenuate ultraviolet components of the light.

What is claimed is:

1. A lighting device, comprising:
   an LED configured to emit white light;
   a collimator;
   a plurality of optical filters; and
   a power supply;
   wherein the plurality of optical filters is disposed between the collimator and the LED;
   wherein the plurality of optical filters are disposed on a support member, the support member configured to rotate about an axis of the lighting device;
   wherein the plurality of optical filters includes a first optical filter and a second optical filter, the first and second optical filters having different transmission coefficients and being positionable to filter the white light emitted by the LED individually, so as to modify the color temperature of the white light emitted by the LED;
   wherein the power supply varies a power supply current supplied to the LED based on whether the first optical filter or the second optical filter is positioned to filter the white light emitted by the LED;
   wherein at least one of the first and second optical filters attenuates a blue component of the white light emitted by the LED at a wavelength lying in the range 400 nm to 480 nm, a color rendering index of the white light emitted by the LED staying in a range of 85 to 100;
   wherein the transmission coefficient of the first optical filter and the second optical filter is one of 96%±2% for wavelengths shorter than 700 nm, 83%±2% for wavelengths in the range of 400 nm to 480 nm, and 64%±2% for wavelengths in the range of 400 nm to 480 nm; and
   wherein the transmission coefficient of the first optical filter and the second optical filter is 2% or less for a wavelength in the ramie of 730 nm to 780 nm.

2. The lighting device according to claim 1, wherein at least one of the first and second optical filters is suitable for attenuating a red component of the light emitted by the LED.

3. The lighting device according to claim 2, wherein both of the first and second optical filters are suitable for attenuating a blue component of the light emitted by the LED at a wavelength lying in the range 400 nm to 480 nm.

4. The lighting device according to claim 3, wherein the first and second optical filters have progressive transmission coefficients for attenuating the blue component.

5. The lighting device according to claim 4, wherein the attenuation difference between the first and second optical filters is at least 15%.

6. The lighting device according to claim 1, wherein the first and second optical filters are arranged at the periphery of the support member.

7. The lighting device according to claim 1, wherein the support member is a rotary disk.

8. The lighting device according to claim 1, wherein at least one of the first and second optical filters is configured to attenuate red components of the white light in the range of 600 nm to 700 nm.

9. A lighting device, comprising:
   an LED configured to emit white light;
   a collimator;
   a plurality of optical filters; and
   a power supply;
   wherein the plurality of optical filters is disposed between the collimator and the LED;
   wherein the plurality of optical filters are disposed on a support member, the support member configured to rotate about an axis of the lighting device;
   wherein the plurality of optical filters includes a first optical filter and a second optical filter, the first and second optical filters having different transmission coefficients and being positionable to filter the white light emitted by the LED individually, so as to modify the color temperature of the white light emitted by the LED;
   wherein the power supply varies a power supply current supplied to the LED based on whether the first optical filter or the second optical filter is positioned to filter the white light emitted by the LED;
   wherein a quantity of light flux leaving the LED and lighting an illuminated field when the first optical filter is positioned to filter the white light, and a quantity of light flux leaving the LED and lighting the illuminated field when the second optical filter is positioned to filter the white light, remain substantially constant relative to each other;
   wherein the transmission coefficient of the first optical filter and the second optical filter is one of 96%±2% for wavelengths shorter than 700 nm, 83%±2% for wavelengths in the range of 400 nm to 480 nm, and 64%±2% for wavelengths in the range of 400 nm to 480 nm; and
   wherein the transmission coefficient of the first optical filter and the second optical filter is 2% or less for a wavelength in the range of 730 nm to 780 nm.

10. The lighting device according to claim 9, wherein the first and second optical filters are light-attenuating optical filters that attenuate a blue component of the white light emitted by the LED.

11. The lighting device according to claim 9, wherein at least one of the first and second optical filters is configured to attenuate red components of the white light in the range of 600 nm to 700 nm.

12. The lighting device according to claim 9, wherein the quantity of light flux leaving the LED and lighting the illuminated field when the first optical filter is positioned to filter the white light, and the quantity of light flux leaving the LED and lighting the illuminated field when the second optical filter is positioned to filter the white light, remain within 5% of each other.

* * * * *